United States Patent [19]
Vachtsevanos et al.

[11] Patent Number: 5,936,665
[45] Date of Patent: Aug. 10, 1999

[54] AUTOMATED APPARATUS FOR COUNTING PILLINGS IN TEXTILE FABRICS

[75] Inventors: George J. Vachtsevanos, Marietta, Ga.; Iqbal M. Dar; Waqar Mahmood, both of Odenton, Md.

[73] Assignee: Georgia Tech Research Corporation, Atlanta, Ga.

[21] Appl. No.: 08/859,443

[22] Filed: May 20, 1997

Related U.S. Application Data

[60] Provisional application No. 60/017,702, May 22, 1996.

[51] Int. Cl.⁶ ........................................................... H04N 7/18
[52] U.S. Cl. ................................. 348/91; 348/92; 348/88; 348/125; 382/111; 382/141; 364/469.01; 364/470.01
[58] Field of Search .................................. 348/86, 88, 91, 348/92, 125, 128, 138; 382/108, 111, 141, 144, 165, 170, 192, 194, 209, 224; 364/469.01, 470.01, 470.14, 470.15; H04N 7/18

[56] References Cited

U.S. PATENT DOCUMENTS

| 4,791,481 | 12/1988 | Verdiere et al. | 348/88 |
| 5,383,135 | 1/1995 | Shofner et al. | 364/470.14 |
| 5,544,256 | 8/1996 | Brecher et al. | 382/149 |
| 5,751,834 | 5/1998 | Lisk, Jr. | 382/111 |

Primary Examiner—Vu Le
Attorney, Agent, or Firm—Harness, Dickey & Pierce, P.L.C.

[57] ABSTRACT

An automated system and associated method of counting pillings in textile fabrics. Images of consecutive sections of a fabric sample are captured by a CCD camera. A system processor then processes the images to enhance image quality. Pillings on the processed, captured fabric sample images are counted, and the resulting data is fuzzified to determine the membership of the data in one or more of a plurality of fabric classes. The present invention provides an objective rating system and method with repeatable accuracy for fabric samples that eliminates the inherent subjectivity associated with conventional manual visual fabric inspection methods.

23 Claims, 7 Drawing Sheets

Radon transform at 90 degrees

Radon Transform after Morphological Filtering

Detrending of the Filtered Signal

Detected Pillings

Pilling Mask for Next Image

Histograms of Classes

Pilling Count

AUTOMATED APPARATUS FOR COUNTING PILLINGS IN TEXTILE FABRICS

CROSS-REFERENCE TO RELATED APPLICATION

This application is based upon and claims priority to United States Provisional Patent Application Ser. No. 60/017,702 filed May 22, 1996, and entitled Automated Apparatus for Counting Pillings in Textile Fabrics, the specification and drawings of which are herein expressly incorporated by reference.

BACKGROUND Of THE INVENTION

1. Technical Field

The present invention relates generally to quality control systems and more particularly to new imaging, data processing, signal processing and fuzzy logic-based techniques as applied to an apparatus and method for counting automatically the number of pillings present in fabric samples for quality control purposes.

2. Discussion

Textile fabrics vary widely in thickness, texture and color patterns. To insure the quality of such fabrics, textile manufacturers utilize human inspectors to manually inspect samples of finished bolts of fabric. These inspectors utilize a rating system to classify the samples, with Class 1 rating being the lowest, or poorest quality rating and Class 5 rating being the highest, or best quality rating.

One of the major areas of concern for textile manufacturers is the number of pillings associated with a particular piece of fabric subsequent to the fabric being subjected to repeated washings. From a quality control standpoint, different types of fabric have different associated acceptable pilling counts. Typically, the more pillings present on the surface of the fabric, the lower the quality of the fabric.

Inspectors have for years used a subjective visual inspection method of determining the rating of these pieces of fabric. Human error is inherently introduced into such a system, as inspectors must subjectively determine the quality of the fabric through their own visual inspection. As a result, different inspectors may have their own individual idea of what constitutes a Class 1 rating, Class 2 rating, Class 3 rating, Class 4 rating, or Class 5 rating. Therefore, a single piece of fabric may be given a different rating by each of the several inspectors rating that piece of fabric. Inherently, such a rating system tends to produce inconsistent quality control results.

Therefore, what is needed is an apparatus and method for producing a more objective analysis of textile fabrics to ensure more consistent quality control ratings for the fabrics, and therefore a better overall quality control system.

SUMMARY OF THE INVENTION

The present invention overcomes the above-mentioned limitations by providing an apparatus and method for automatically counting the number of pillings on textile fabrics. The present invention provides an apparatus and corresponding software with minimal set-ups; an imaging and data processing software procedure for counting the number of pillings; and a methodology for classifying the fabric samples into one of the pre-defined classes with repeatable accuracy while accounting for human judgment by allowing the determination of the degree of confidence assigned to the sample's membership in each class.

The present invention utilizes a CCD array camera for detecting pillings on a sample bolt of fabric mounted on a fabric sample feeding mechanism and rotated by a driver stepper motor. The apparatus employs two possible configurations with the first one using an ultraviolet (UV) light source and dark background for light color samples and the second using a neon light source and white background for dark colored samples. Processing software requires as input the relative thickness of the fabric for necessary adjustments of the windowed image.

The camera captures successive images of the fabric sample as the sample is rotated via the controlled driving mechanism exposing consecutive sections of the fabric samples to the camera's field of view. These images are processed to count the number of pillings on the sample fabric. Counts thus obtained through repeated experiments on a large number of samples are used to develop fuzzy membership functions corresponding to five quality classes accepted as standards in the textile industry. Expert operators (inspectors) are used to classify the test fabric samples into one of five quality classes. A histogram is developed first from this statistical data and converted to fuzzy membership functions. A count obtained for a new sample is fuzzified and represents the membership of the sample to various classes. Thus, through the use of fuzzy logic, the captured image data is processed and compared to historical fuzzy distributions stored as templates in a computer. The fuzzy membership function for the sample tested models is compared to the subjective judgment of experienced operators and the fabric is then given a class rating of 1 to 5 based on this fuzzy logic-based comparison. If the fuzzy membership functions of the tested sample overlaps more than one of the five template distributions, then a degree of confidence is assigned to signify the extent of its membership to each overlapping class.

DETAILED DESCRIPTION OF THE PREFERRED EMBODIMENTS

Figure 1:
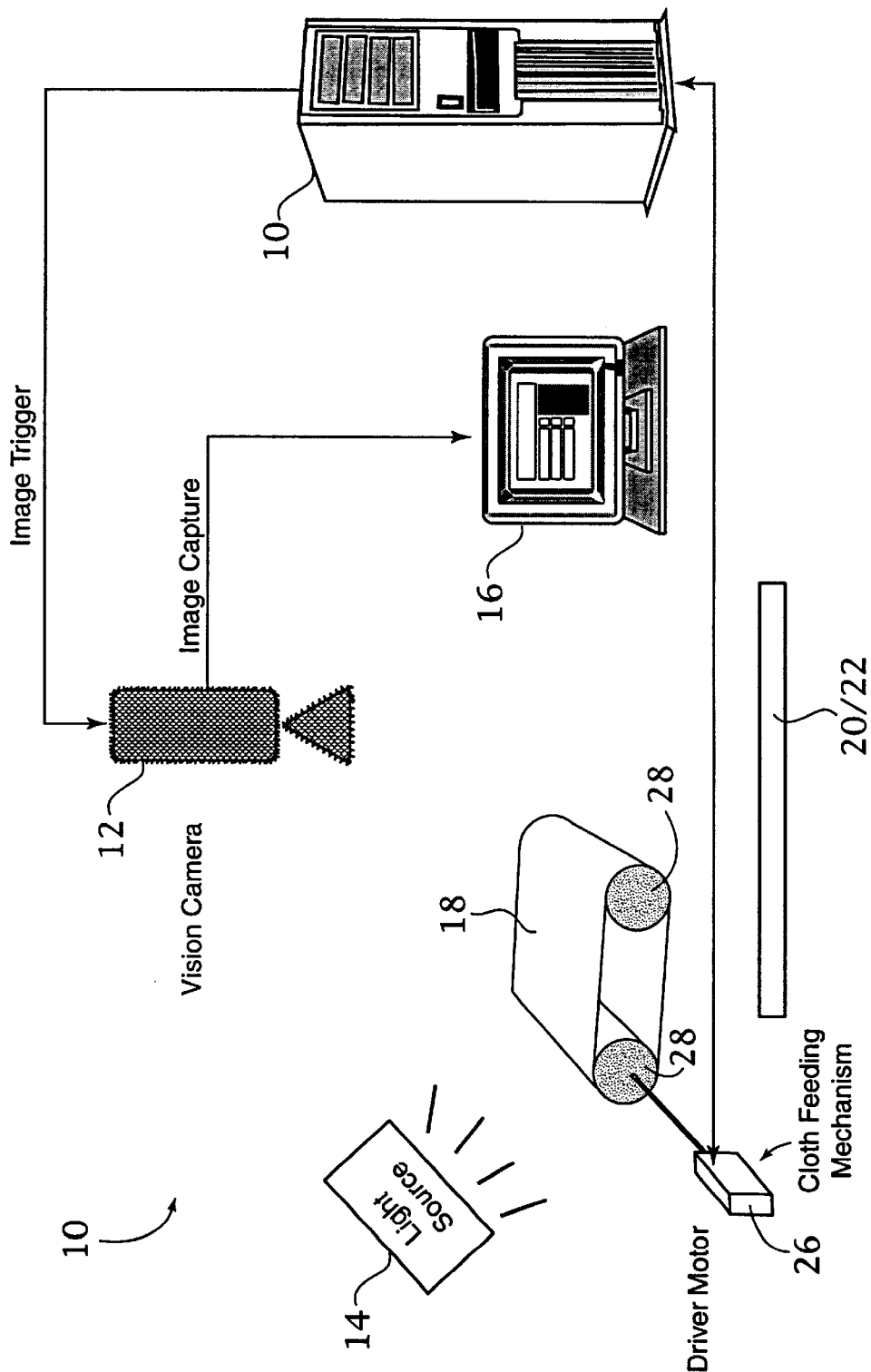
FIG. 1 illustrates system components in a preferred embodiment of the present invention.

Referring now to the drawings, FIG. 1 illustrates an automatic pilling detection system generally at 10. As will be described in detail below, the system 10 is implemented through both hardware and software to count the number of pillings associated with a sample fabric in a manner that gives consistent results for fabrics of a variety of colors and textures. The system 10 thereby gives a high degree of objectivity to a quality control system that has historically been implemented through visual checking of the fabric by human inspectors, and thus which thereby has a very high degree of associated subjectivity.

Hardware

The automatic pilling detection system of the present invention involves application and integration of a state of the art machine vision system, automated fabric feed mechanism, and a processor for computation and control purposes, as will now be described in more detail.
Vision System The vision system consists of a Pulnix CCD gray scale camera 12 having a Cannon 16–100 mm variable zoom lens with 1.25 in×1.25 in field-of-view and 640 pixel by 480 pixel resolution. An ultra-violet (UV) light source 14 is used with the camera for front directional illumination. An image grabber 16 with thirty frames/second translation is also implemented with the camera lens. The variable zoom lens and camera are used to finalize the field of view, depth of field, and focal length. These parameters may be adjusted once so that the image resolution for pilling detection of a particular type of fabric such as the fabric shown at 18 satisfies a specified lower bound. Flexibility for such parameter adjustment has been provided in the camera and light mounting system. More than one camera may be used to capture a longer image.
Ultra-Violet Light Source The directional illumination ultra-violet light source 14 was selected after experimentation with different types of light sources including diffused light, goose necks, back-lighting, and front-lighting. UV light provides the best contrast between the image of the fabric 18 and the background. A good reflector 20 for UV light is used as a background for dark colored fabric, and a good absorbent 22 is used for light colored fabric.
Image Grabber The data translation image grabber 16 is used for on-line capturing of the image. A two dimensional 256 gray scale image of the fabric sample is recorded. A number of image processing steps are performed over the captured image for correct determination of the pilling count as discussed in the software description below.
Feed Mechanism The fabric feed mechanism consists of a feed forward/backward stepper motor 26 operatively connected to a rotatable mounting 28 to which the fabric sample is affixed. The mounting is controlled by a RS232 compatible position controller. The fabric feed mechanism is adjusted so that a correct pilling count is obtained with minimum stepping of the feed mechanism. A provision in the control logic is provided for adjustment of the feed step size as it may require changes for various fabric types. Another important feature of the control logic is the generation of a mask for each image which prevent pillings to be counted more than once in consecutive images.

A 90 M Hz pentium machine 30 with 16 MB RAM is preferably used as a platform for image processing, control and coordination of the feed mechanism and vision system. All image processing and control methods are developed in Borland C. The front end of the system used by the operator consists of graphical displays indicating different logical steps of the pilling count apparatus and method of the present invention. It also prompts the operator for simple key in operations for one time positioning of the motor, light, and camera at correct locations at the start of the automatic count procedure.

Software

Figure 2:
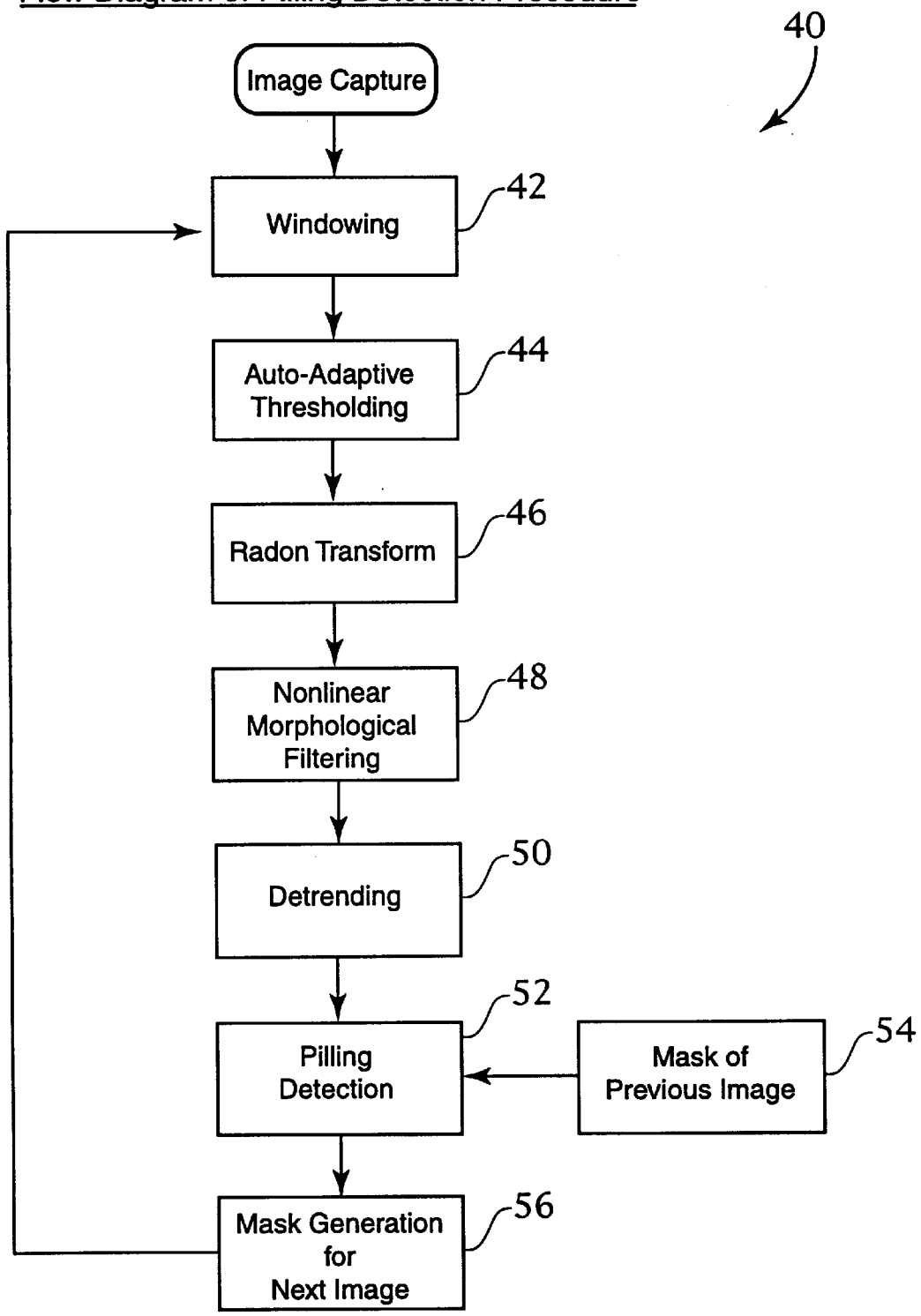
FIG. 2 illustrates a flow diagram illustrating the steps involved in implementing the automatic pilling detection procedure according to a preferred embodiment of the present invention.
Figure 3:
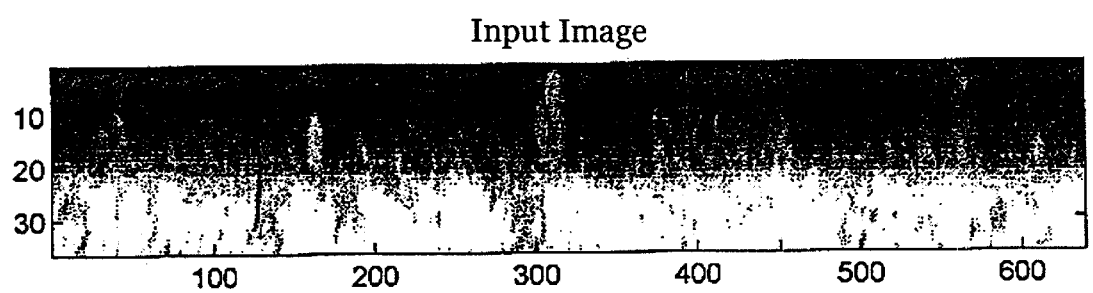
FIG. 3 is a graphical representation of the input image captured by the system camera and input into the system processor.
Figure 4:
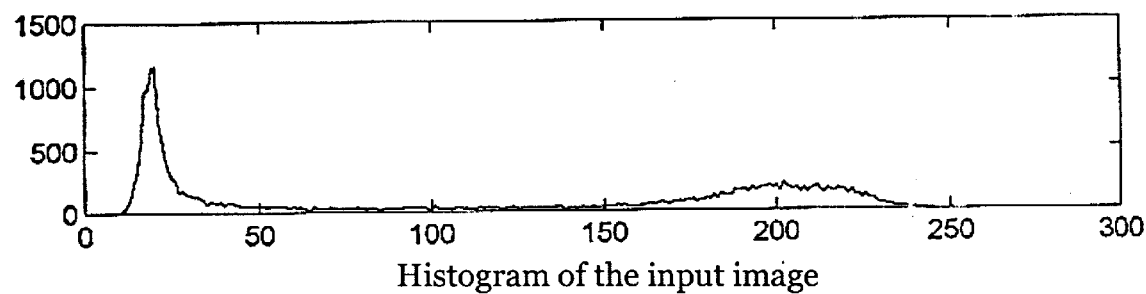
FIG. 4 illustrates a histogram of the input image shown in FIG. 3.
Figure 5:
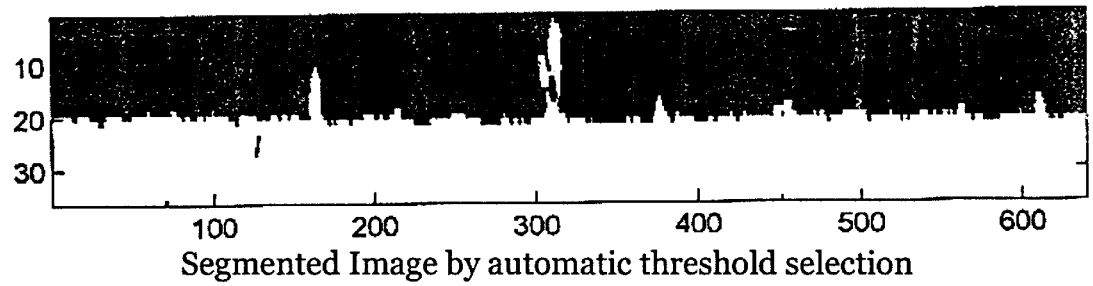
FIG. 5 illustrates a segmented portion of the input image shown in FIG. 3.
Figure 6:
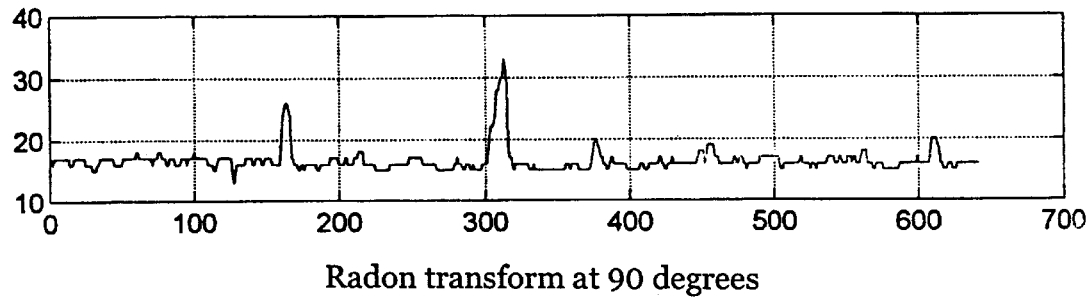
FIG. 6 illustrates a radon transform of the segmented image shown in FIG. 5.
Figure 7:
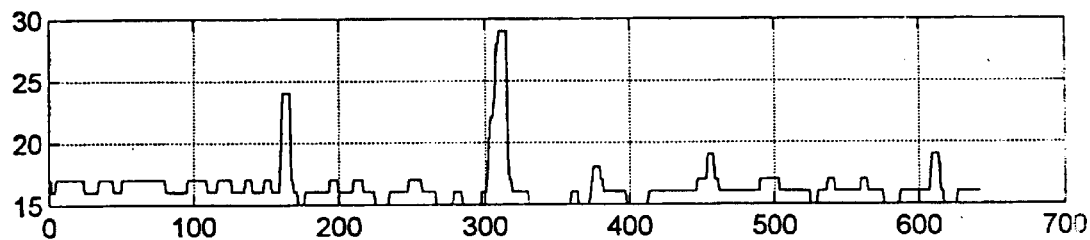
FIG. 7 illustrates the radon transform of FIG. 6 after morphological filtering.
Figure 8:
FIG. 8 illustrates a graphical representation of the data in FIG. 7 subsequent to detrending of the data.
Figure 9:
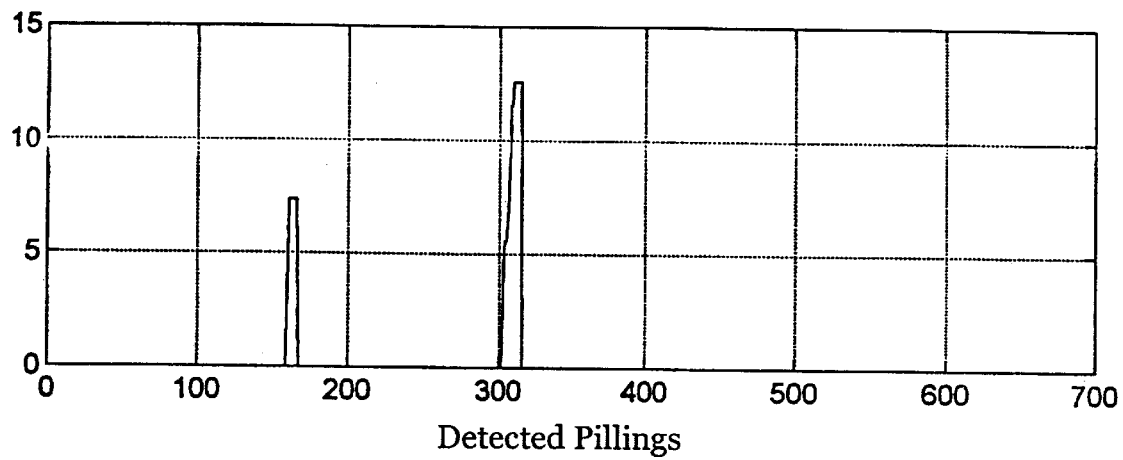
FIG. 9 illustrates a graphical representation of the detected pillings determined from the input image shown in FIG. 3.

With reference to the flow diagram 40 in FIG. 2, the various logical steps involved in automatic detection of fabric pillings programmed into the system processor are described below:
Image Capturing At step 42, a two dimensional, 256 gray scale image of the fabric is captured using the CCD camera. A sample image is shown in FIG. 3. An ultra violet light source is used as front directional illumination.
Windowing At step 44, a pre-programmed rectangular window is used to select the region of interest in the captured image with the 640×480 pixel resolution camera. The window is preferably 640×50 pixels. However, the window dimensions may be varied according to the particular application. For the rest of the processing steps, the selected region of the image, called sub-image, is used.
Auto-Adaptive Threshholding Referring to FIGS. 4 and 5, at step 44, a histogram analysis, such as that represented in FIG. 4, is performed on the sub-image, and a threshold value is determined automatically. The threshold value selection accommodates the illumination variations as long as a good contrasted image can be captured. The calculated threshold value, shown in FIG. 5, is then used to segment the sub-image into the background and the fabric.
Radon Transforming At step 46, the radon transform converts a two-dimensional image into a one-dimensional signal by taking the integral of the two-dimensional image along a specified direction. For pilling detection, the radon transform is applied along the vertical direction of the segmented sub-image as shown graphically in FIG. 6.
Nonlinear Morphological Filtering At step 48, to filter out the noise from the radon transformed sub-image, a nonlinear morphological filter has been designed. This filter performs a series of erosion and dilation operations on the radon transformed signal. The resulting signal is shown in FIG. 7. The structuring element for these morphological operations is designed such that fuzz balls (which are not pillings) are filtered out.
Detrending Referring to step 50, sometimes the fabric is not uniform along the full length of the roller. This is common for thick fabrics and may result in an incorrect pilling count. As shown in FIG. 8, detrending is performed to remove the non-uniform mounting effect from the morphologically filtered signal. This is done by subtracting the linear trend from the morphologically filtered signal. A least square estimation is performed to determine the linear trend of the signal.
Pilling Detecting Referring to FIG. 9 at step 52, pillings are detected by counting the connecting segments of the detrended signal above a pre-determined threshold. The value of this threshold depends upon the smallest pilling which must be determined.

Mask Generating

Figure 10:
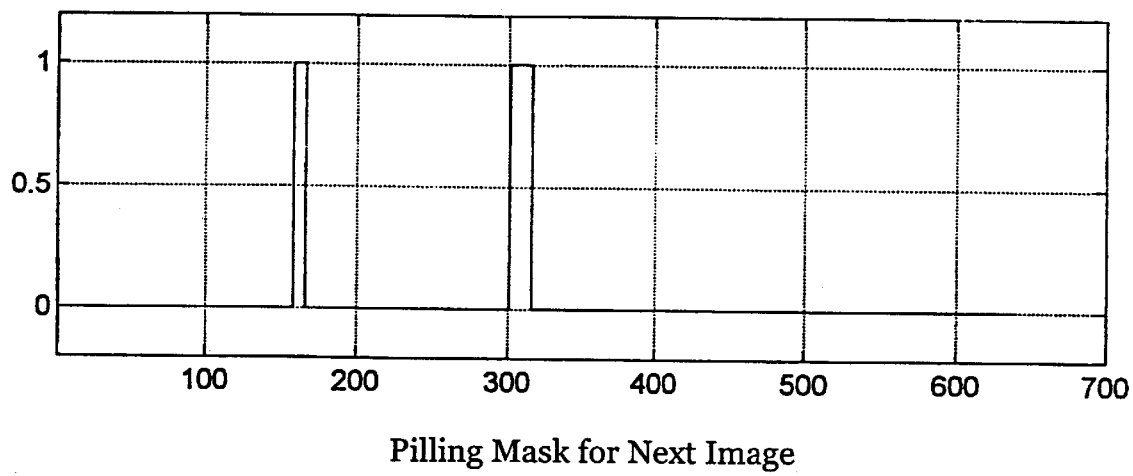
FIG. 10 illustrates pilling mask for the next image taken by the image camera of the sample fabric.
Figure 11A:
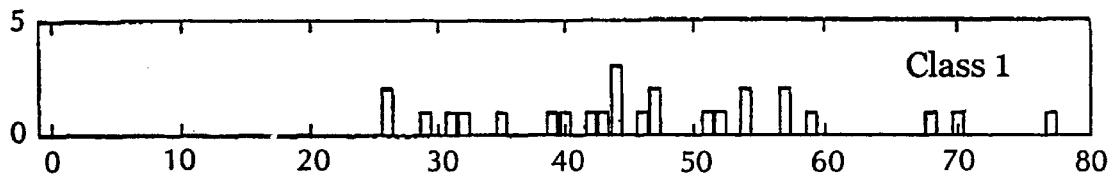
FIGS. 11a through 11e are histograms of historical occurrences of Class 1–Class 5 ratings, respectively, for pilling counts of the fabric samples as selected by human inspectors and as determined by the present invention.
Figure 11B:
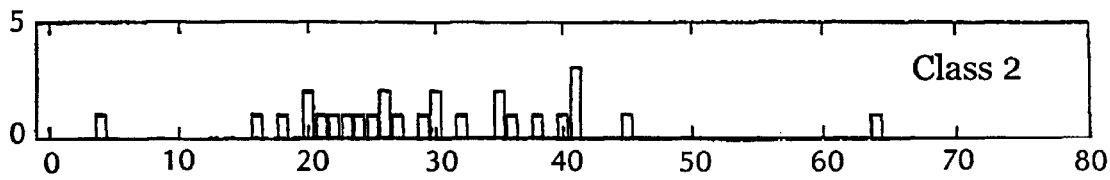
Figure 11C:
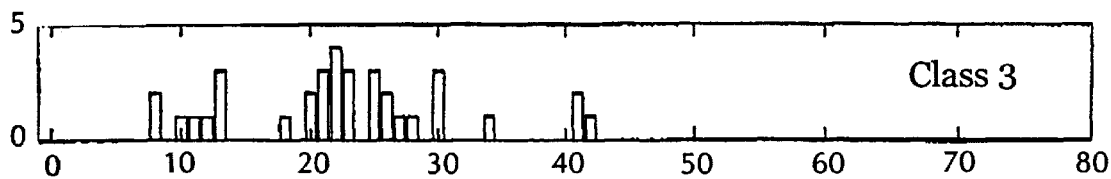
Figure 11D:
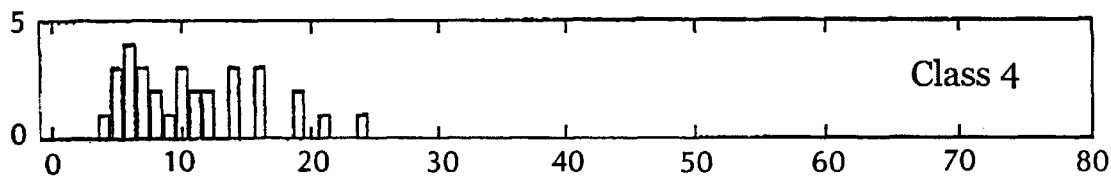
Figure 11E:
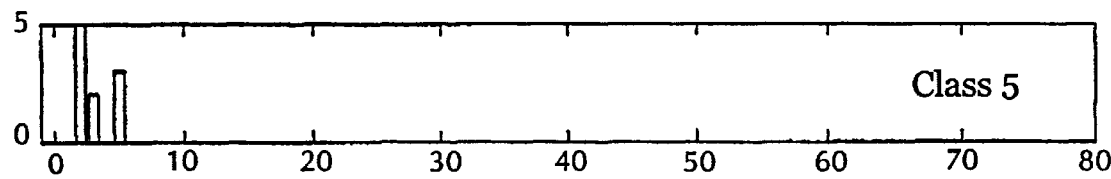

Referring to FIG. 10, a mask is generated for each sub-image. The mask of a sub-image represents the location of the detected pillings. To determine the total number of pillings on the fabric, it is sometimes possible that a pilling be viewed more than once but should be counted only once in total count. As indicated at step 54, the mask of the current image is compared with the mask of the previous image. Pillings found at the same location in both images are counted only once. Subsequently, a mask is generated from the next image as indicated at step 56.

Fabric Rating

Once the pilling count has been found after the above-mentioned software steps, the pilling count is fuzzified to represent the membership of the sample to fabric ratings of 1 to 5. Referring to FIG. 11, a distribution of actual pilling counts obtained by the present invention for numerous manually classified samples is shown. Such ratings data represents the data typically input into and stored by the system database. The fuzzy class membership if assigned to a sample piece of fabric according to the pilling count detected and based on the human classification available in the historical database, as will now be described.

As shown in the histogram in FIG. 11, a specific pilling count may historically have been given different ratings for a particular type of fabric sample. For example, referring to the histogram in FIG. 11a, human inspectors have given a Class 1 rating to fabric samples when a pilling count has ranged from about 25 to almost 80 pillings. Referring to the histogram in FIG. 11d, inspectors have given fabric samples a Class 3 rating when the pilling count has ranged from about 8 to almost 42. These histograms thus illustrate the inconsistent results of the conventional method of subjective human visual inspection of fabric samples.

Figure 12:
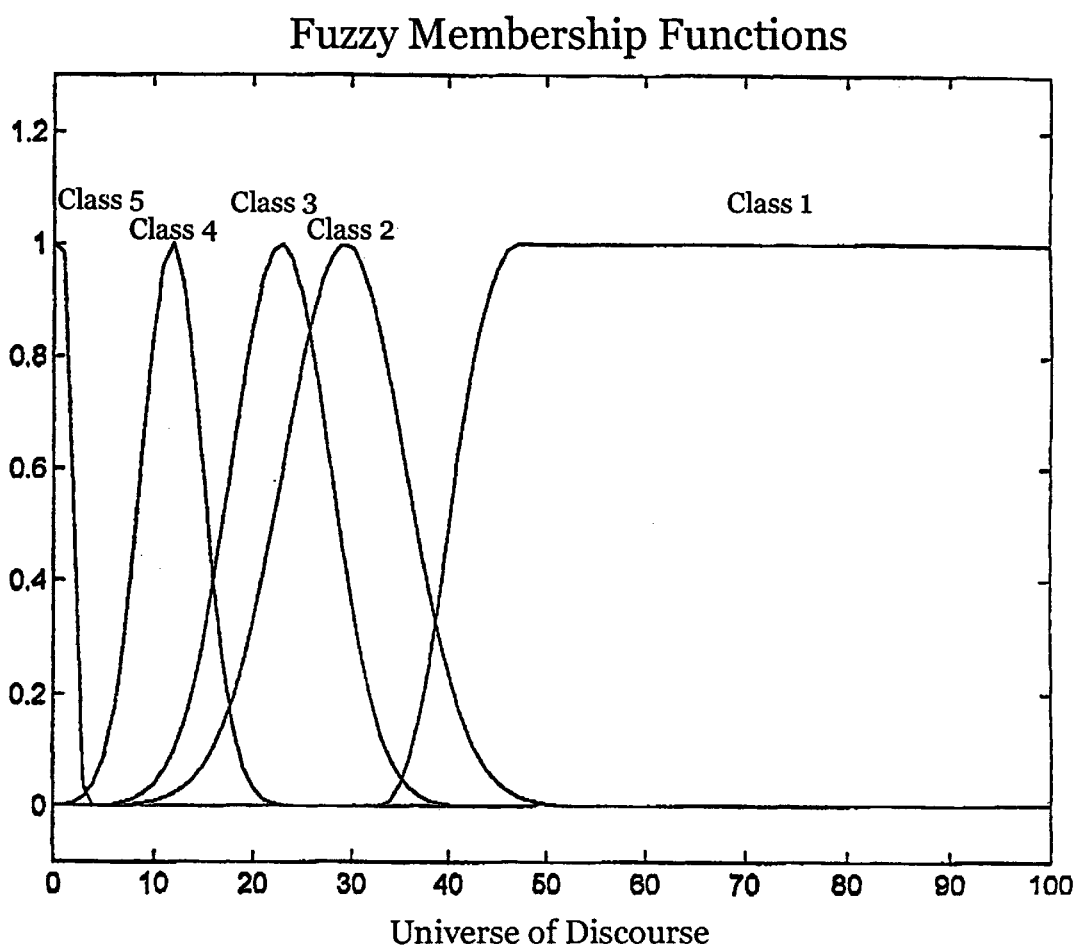
FIG. 12 is a representation of fuzzy membership functions. The universe of discourse of the memberships is the pilling count. The figure illustrates the membership function for the five classes over the universe of discourse.

Referring to FIG. 12, the system of the present invention assigns a fuzzy membership to the five classes, indicated along the left of the graph in FIG. 12, to each pilling count value indicated along the bottom of the graph. For example, for a pilling count 15, a membership of about 0.4 is given to Class 4 rating, a membership of about 0.4 is given to a Class 3 rating, and a membership of about 0.2 is given to a Class 2 rating. Similarly, for a pilling count of 30, a membership of 0.35 is given to a Class 3 rating and a membership of about 0.9 is given to a Class 2 rating. This fuzzy membership value represents the degree of confidence associated with a certain classification. Thus, for a pilling count of 30, the degree of confidence associated with Class 2 is 0.9 while it is only 0.35 for Class 3. The degree of confidence for Classes 1, 4 and 5 is zero for this case.

A look-up table implemented at the system controller is utilized to determine the overall sample class rating given the fuzzy membership values for Classes 1–5 associated with the sample. The overall sample class ratings for fabrics of various textures can be programmed into the controller in accordance with particular quality control needs.

While the above description constitutes the preferred embodiment of the present invention, it should be appreciated that the invention may be modified without departing from the proper scope or fair meaning of the invention.

I claim:

1. A pilling detection system, comprising:
   a pilling detection device that detects pillings which are distributed across a fabric sample;
   a feed mechanism that provides the fabric sample to the pilling detection device at a predetermined feed rate; and
   a processor that controls the predetermined feed rate of the feed mechanism and that assigns a class rating to the fabric sample based on comparing the number of pillings detected by the pilling detection device to stored historical classification data, said processor being programmed with fuzzy logic to determine said class rating based upon how said pillings are distributed across said fabric sample.

2. The pilling detection system of claim 1, wherein the stored historical classification data comprises a plurality of fuzzy membership values that represents historical classifications for a plurality of fabric samples of like color and texture.

3. The pilling detection system of claim 2, wherein the stored historical classification data further comprises a plurality of histograms programmed into the processor that represent a range of pilling counts associated with the plurality of sets of fuzzy membership values.

4. The pilling detection system of claim 2, further comprising a plurality of sets of fuzzy membership values each representing historical classifications for a plurality of fabric samples of like color and texture.

5. The pilling detection system of claim 4, wherein the stored historical classification data further comprises a plurality of histograms programmed into the processor that represent a range of pilling counts associated with each of the plurality of sets of fuzzy membership values.

6. The pilling detection system of claim 2, further comprising a look-up table programmed into the processor that enables the processor to determine a class rating for the test fabric sample based on a comparison of the fuzzy membership values for the number of pillings detected by the pilling detection device with predetermined quality control requirements.

7. The pilling detection system of claim 1, wherein the pilling detection device comprises a charge coupled device (CCD) array camera.

8. The pilling detection system of claim 7, further comprising a light source associated with the CCD camera that illuminates the test sample fabric for image resolution purposes.

9. The pilling detection system of claim 8, wherein the light source is an ultraviolet light source that illuminates dark-colored fabric samples.

10. The pilling detection system of claim 8, wherein the light source is a neon light source that illuminates light-colored fabric samples.

11. The pilling detection system of claim 1, further comprising an image grabber associated with the processor that records a gray scale image of the test sample fabric for pilling count purposes.

12. The pilling detection system of claim 11, wherein the processor generates a mask for each recorded gray scale image to prevent pillings from being counted more than once in consecutively recorded images.

13. The pilling detection system of claim 11, wherein the feed mechanism is operatively coupled to the image grabber and is adjustable so that a correct pilling count is obtained with minimum stepping of the feed mechanism.

14. The pilling detection system of claim 1, wherein the pilling detection device comprises a camera that has a predetermined field of view and pixel resolution.

15. An automated method for counting fabric pillings, comprising the steps of:

capturing images of consecutive sections of a fabric sample, said pillings being distributed across said fabric sample;

processing the captured images to enhance image quality;

counting pillings on the processed, captured fabric sample images; and comparing the counted pillings to stored quality control data to provide an objective rating of the fabric sample with repeatable accuracy based upon how said pillings are distributed across said fabric sample.

16. The method of claim 15, wherein the step of comparing the counted pillings to stored quality control data comprises the step of comparing the counted pillings to stored historical pilling count data for a plurality of like fabric samples.

17. The method of claim 16, wherein the step of comparing the counted pillings to stored historical pilling count data comprises the step of:

assigning a fuzzy membership value to the pilling count for each of a plurality of class ratings.

18. The method of claim 15, wherein the step of processing the captured images comprises the steps of:

selecting a sub-image within a region of a captured image;

determining a sub-image threshold value to segment the sub-image into a background two-dimensional sub-image and a fabric two-dimensional sub-image;

transforming the fabric two-dimensional sub-image into a one-dimensional sub-image;

filtering noise from the transformed one-dimensional fabric image; and detrending the filtered one-dimensional fabric image to account for thickness variations in the fabric sample.

19. The method of claim 18, wherein the step of counting pillings on the processed, captured fabric sample image comprises the step of:

counting the connecting segments of the detrended, filtered one-dimensional image above a pre-determined threshold.

20. The method of claim 19, further comprising the steps of:

generating a mask for the sub-image after the step of counting the connecting segments; and comparing a mask of a current image with a mask of a previous image to ensure that same location pillings are counted only once.

21. The method of claim 15, wherein the step of comparing the number of pillings counted to stored quality control data comprises the step of implementing fuzzy logic to provide an objective rating of the sample fabric based on historical subjective ratings of like fabric samples.

22. An automated apparatus for counting pillings in textile fabrics, comprising:

a pilling detection device that detects pillings which are distributed across a fabric sample;

a feed mechanism that provides the fabric sample to the pilling detection device at a predetermined feed rate;

a processor programmed with fuzzy logic to compare the detected pilling count as distributed across said fabric sample to historical fuzzy distributions stored in the processor, assign a degree of confidence to signify the extent of membership of the pilling count to any overlapping fuzzy distributions, and assign a class rating to the sample fabric based on the extent of membership of the pilling count to overlapping fuzzy distributions and quality control parameters programmed into the processor.

23. An automated method of counting pillings in textile fabrics, comprising the steps of:

capturing images of consecutive sections of a fabric sample, said pillings being distributed across said fabric sample;

processing the captured images to enhance image quality;

counting pillings on the processed, captured fabric sample images; and fuzzifying data generated from the step of counting pillings to determine the membership of the data in one or more of a plurality of fabric classes based upon how said pillings are distributed across said fabric sample.

* * * * *